United States Patent [19]

Ryder et al.

[11] Patent Number: 4,657,870

[45] Date of Patent: Apr. 14, 1987

[54] INCUBATOR OPTICAL SYSTEM FOR VIEWING STERILIZATION INDICATOR

[75] Inventors: Francis E. Ryder; Larry T. Ryder, both of Arab, Ala.

[73] Assignee: Ryder International Corporation, Arab, Ala.

[21] Appl. No.: 603,234

[22] Filed: Apr. 23, 1984

[51] Int. Cl.$^4$ .............................................. C12M 1/12
[52] U.S. Cl. .................................. 435/311; 435/287; 356/246; 356/440
[58] Field of Search .................... 422/64, 101, 102; 435/291, 293, 294, 300, 301, 808, 809; 356/246, 409, 440, 441

[56] References Cited

U.S. PATENT DOCUMENTS

| Re. 28,801 | 5/1976 | Acker et al. | 356/440 |
|---|---|---|---|
| Re. 30,391 | 9/1980 | Liston | 356/409 |
| 1,644,330 | 10/1927 | Exton | 356/441 X |
| 2,288,143 | 6/1942 | Sheppard | 356/440 X |
| 3,383,917 | 5/1968 | Ryder | 73/327 |
| 3,417,614 | 12/1968 | Ryder | 73/327 |
| 3,417,615 | 12/1968 | Ryder | 73/327 |
| 3,508,804 | 4/1970 | Müller | 350/19 |
| 3,597,972 | 8/1971 | Ryder | 73/291 |
| 3,597,973 | 8/1971 | Ryder | 73/291 |
| 3,627,431 | 12/1971 | Komarniski | 356/180 |
| 3,661,717 | 5/1972 | Nelson | 195/103 |
| 4,144,030 | 3/1979 | Suovaniemi | 436/165 |
| 4,304,869 | 12/1981 | Dyke | 435/296 |
| 4,498,782 | 2/1985 | Proctor et al. | 356/436 |
| 4,534,651 | 8/1985 | Minikane | 356/440 |

OTHER PUBLICATIONS

Brochure entitled "Attest Biological Monitoring Systems"–3M Corporation–date: unknown.
Brochure entitled "AMSCO Proof Monitoring System"–AMSCO Medical Products–date: unknown.

Primary Examiner—Samuel Scott
Assistant Examiner—Allen J. Flanigan
Attorney, Agent, or Firm—Trexler, Bushnell & Wolters, Ltd.

[57] ABSTRACT

An optical system is provided for viewing a sterilization indicator including a receptacle, the receptacle having a translucent portion and being carried interiorally of an incubator. The optical system comprises a light source, and first light transmission structure located intermediate the light source and the receptacle for redirecting light from the light source through the translucent portion of the receptacle. A viewing window is located in an external surface of said incubator; and second light transmission structure is located on a side of the receptacle generally opposite the first light transmission means for redirecting light transmitted through the translucent portion of said receptacle to the viewing window.

29 Claims, 5 Drawing Figures

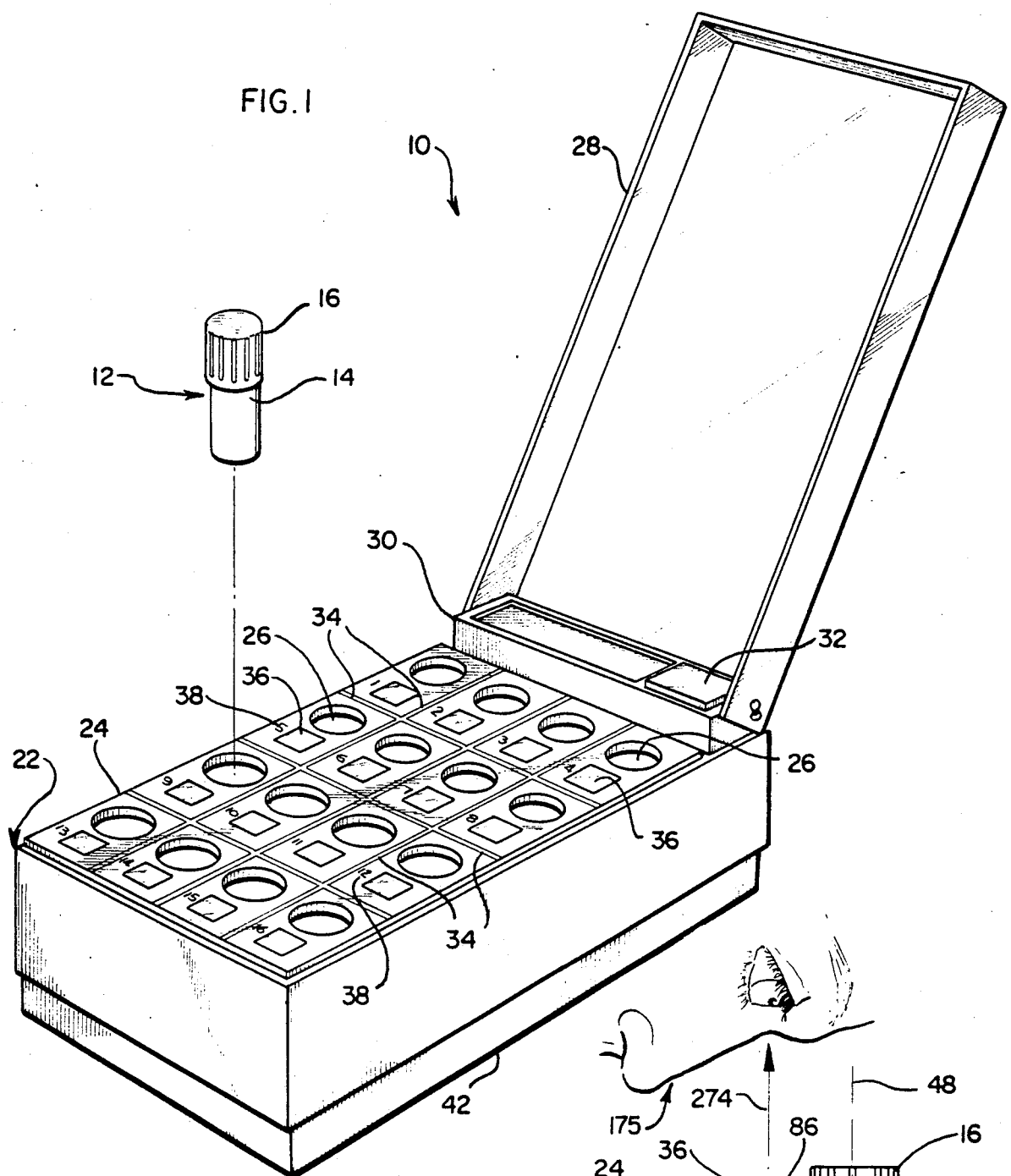
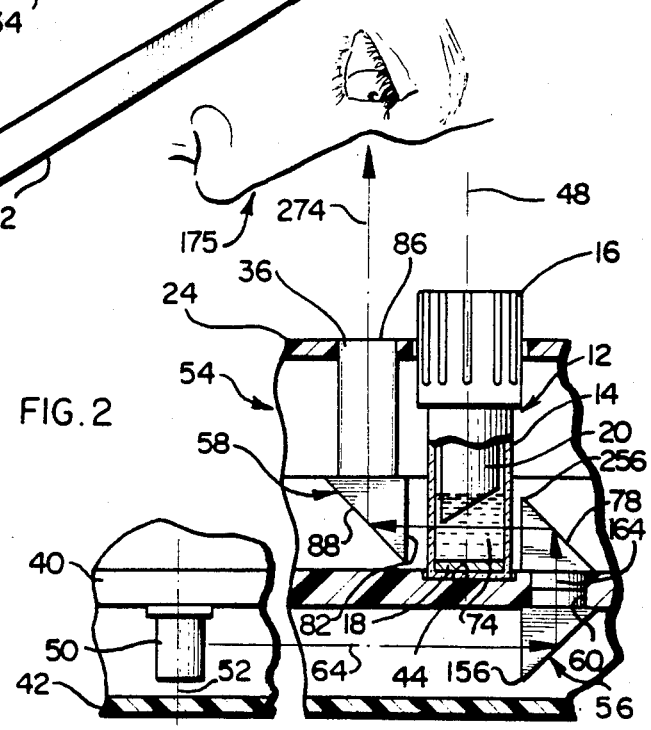
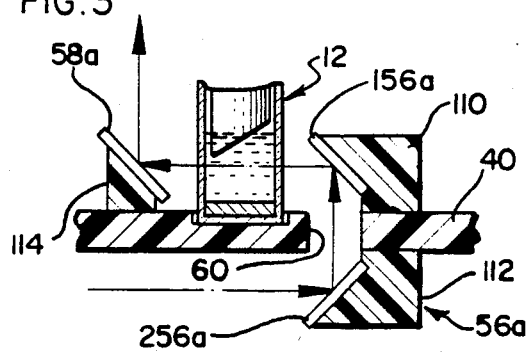
FIG. 1
FIG. 2
FIG. 3

INCUBATOR OPTICAL SYSTEM FOR VIEWING STERILIZATION INDICATOR

BACKGROUND OF THE INVENTION

The apparatus of the present invention relates to an incubator for a biological indicator used to monitor the effectiveness of a sterilization process. More particularly, the invention is directed to an optical viewing system or arrangement for an incubator which facilitates viewing of a sterilization indicator which includes a receptacle.

Such an incubator may be any of a variety of shapes and sizes, but preferably is configured to accept a plurality of such receptacles, for simultaneously incubating the contents of the sterilization indicators. Heretofore, it has been the practice to provide a transparent or translucent portion of the receptacle, so that the contents thereof may be viewed by removing the receptacle from the incubator. However, individual handling and identification of receptacles could be simplified by providing means for viewing the contents of the receptacle while still in the incubator. In this regard, the present invention is directed to a novel optical arrangement or system to enable viewing of the contents of each receptacle while the receptacle remains in the incubator apparatus.

At this point, a brief general description of the structure and use of such a sterilization indicator may prove helpful in understanding the invention.

In order to test the effectiveness of a steam or gas sterilization process, standardized spores of a bacterial strain sufficiently resistant to the sterilization medium are placed on a carrier, such as a spore disc or strip, and the strip is exposed to the sterilization medium being tested, normally gas, steam or dry heat. Destruction of the standardized spore strain insures sterilization of the bacterial strain in the chamber of the autoclave or other sterilization device. On the other hand, the presence or survival of these standardized spore strains indicates an unsatisfactory sterilization process.

After the sterilization process has been completed, the survival of the spores is determined by mixing a test solution containing a culture or growth medium and a pH indicator with the bacterial spores and thereafter incubating the culture for growth. In spore fermentation, for example, glucose contained in the growth medium is utilized by viable or living spores, and pyruvic acid is produced as a byproduct. The pyruvic acid lowers the pH of the test solution and results in a change of color of the pH indicator in the solution. If there are no living or viable spores following sterilization, the pH and the color of the test solution remains essentially unchanged. Hence, the pH indicator in the solution acts as an indication of the effectiveness of the sterilization process.

Various ways are known for mixing the test solution with the strips containing the microorganisms or spores. One such way consists of providing a hermetically sealed glass ampule containing the culture medium and enclosing the ampule and the test strip in a container or receptacle and providing a means to crush the ampule whereby the culture medium floods the test strip in the receptacle. Thereafter, the saturated test strip in the receptacle is incubated for the requisite period of time in order to determine whether or not viable bacteria is present. The receptacle has a transparent or translucent portion to permit viewing of the color of the test solution and pH indicator. Devices of the foregoing type are shown, for example, in U.S. Pat. Nos. 3,440,144; 3,661,717 and 4,304,869.

As previously indicated, the present invention is an improvement on incubator devices or apparatus used in the foregoing procedure. In this regard, it is also desirable to provide an incubator apparatus for handling a plurality of receptacles which is relatively compact and simple to operate. Additionally, it is desirable to provide for simultaneous viewing of the color of the test solution in each of a plurality of receptacles within the incubator. Advantageously, the optical structure or arrangement of the present invention makes possible such simultaneous viewing while maintaining compactness, by arranging a plurality of receiving wells for the receptacles in an array of rows and columns. A convenient viewing window is provided adjacent an entrance aperture or opening to each of these receiving wells. The novel optical system of the invention passes light from a suitable source through a translucent portion of each of the receptacles for viewing the color of the test solution therein at the associated viewing window.

OBJECTS AND SUMMARY OF THE INVENTION

Accordingly, it is a general object of this invention to provide a novel and improved incubator for a sterilization indicator system.

Yet a more specific object is to provide an incubator in accordance with the foregoing objects which employs a novel optical system to facilitate viewing of the contents of a sterilization indicator receptacle without removing the receptacle from the incubator.

A further object is to provide an incubator employing a novel optical structure or system in accordance with the foregoing object which additionally provides simultaneous viewing of the contents of a plurality of sterilization indicator receptacles within the incubator apparatus.

In accordance with the foregoing objects, the present invention provides a novel optical system for viewing a sterilization indicator including a receptacle, said receptacle having a translucent portion and being carried interiorally of an incubator. The optical system comprises a light source, first light transmission means located intermediate said light source and said receptacle for redirecting light from the light source through said translucent portion of said receptacle; a viewing window located in an external surface of said incubator; and second light transmission means located on a side of said receptacle generally opposite said first light transmission means for redirecting light transmitted through said translucent portion of said receptacle to said viewing window.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawing in which like reference numerals identify like elements, and in which:

FIG. 1 is a perspective view of an incubator apparatus in conjunction with a sterilization indicator, and employing a novel optical system in accordance with the invention;

FIG. 2 is an enlarged side elevation, partially broken away and partially in section, illustrating an exemplary portion of the optical system employed in the apparatus of FIG. 1;

FIG. 3 is a view, similar to FIG. 2, of an alternate embodiment of the optical system portion of FIG. 2;

DETAILED DESCRIPTION OF THE ILLUSTRATED EMBODIMENT

Figure 4:
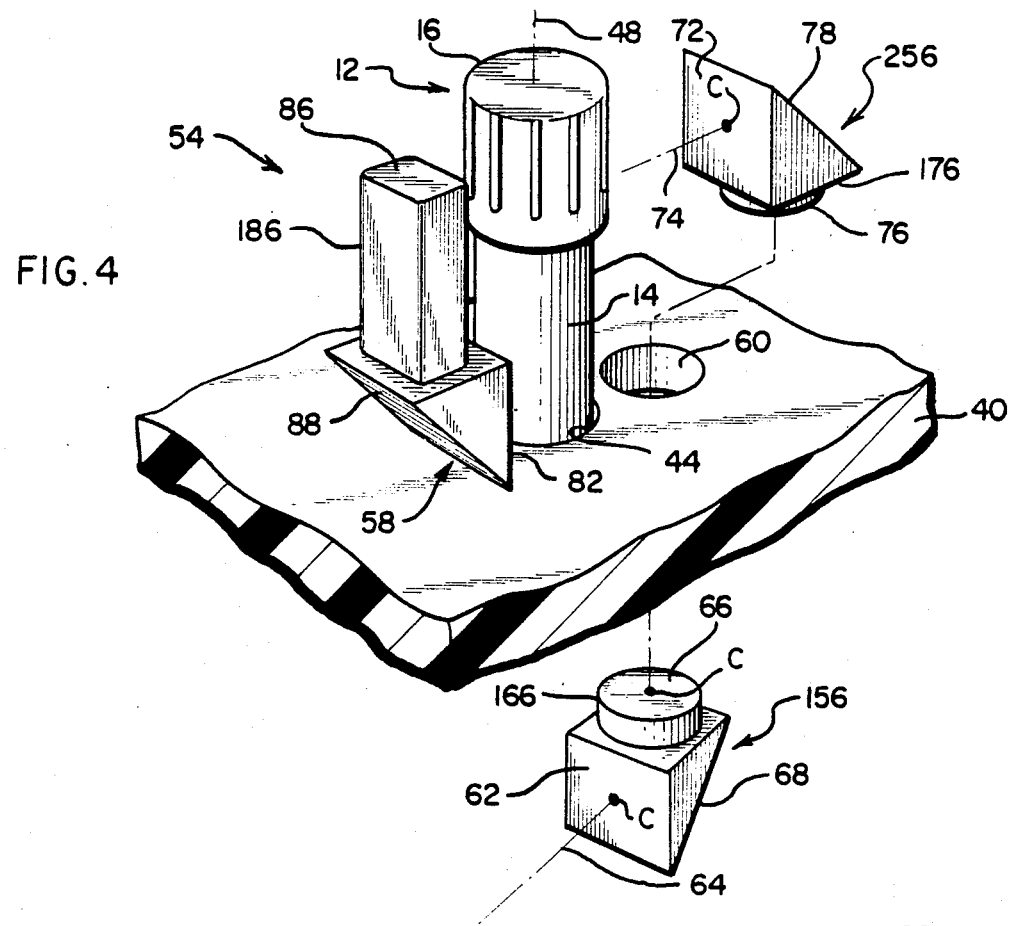
FIG. 4 is an additionally enlarged exploded perspective view further illustrating the structure and operation of the exemplary optical system portion of the embodiment of FIG. 2.

Referring now to the drawings and initially to FIG. 1, an incubator in accordance with the invention is designated generally by the reference numeral 10. As indicated previously, the incubator 10 is intended for incubating a plurality of sterilization indicators, each including a receptacle such as receptacle 12.

The sterilization indicator including receptacle 12 and contents thereof form no part of the present invention. Suffice it to say, that the receptacle 12 includes a preferably translucent or transparent body portion 14 and an interfitting cap or cover portion 16 of somewhat larger diameter.

Referring briefly to FIG. 2, the transparent body 14 forms a chamber which carries a biological spore disc 18 which is of known composition and/or construction and includes a standardized bacterial strain. Also within the chamber defined by body 14 is a breakable or frangible container or ampule (not shown). This cover or cap 16 is axially advanceable with respect to the frangible ampule and includes a biased end surface 20 which projects interiorally of the chamber defined by the receptacle body 14, and is useful in fracturing the ampule (not shown).

The container or ampule (not shown) contains a suitable test solution of known composition, including a nutrient media and a pH indicator. Accordingly, upon advancement of the cap 16, the projection or end surface 20 will break the ampule and cause the indicator solution to flood the container 20 and come into contact with the disc 18.

Thereupon, the receptacle 12 is placed into the incubator 10 of the invention for incubation in known fashion, whereupon the contents of the transparent receptacle body 14 will remain essentially colorless or change color, in accordance with known practice, thereby indicating the effectiveness of the sterilization process upon the bacterial spores carried on the disc 18.

Returning now to the incubator structure of the invention, it will be seen that the incubator 10 of FIG. 1 comprises a housing 22 which has a top surface 24 formed with a plurality of through apertures or openings 26, each for receiving one such receptacle 12 therethrough, as best viewed in FIG. 2. In the preferred embodiment illustrated, an additional transparent cover 28 is also hingedly mounted to provide an additional closure for the top surface 24 of the housing 22 and the plurality of receptacles 12 which may be inserted therein. To this end, it will be noted that the cover 28 is hingedly mounted to an upwardly projecting portion 30 of the housing 24 to accommodate the upwardly projecting portions of the covers or cap members 16 of these receptacles 12. This projecting surface or portion 30 may also be provided with a suitable indicator or lamp 32 to indicate whether power to the unit is on or off.

The top surface 24 is also provided with suitable indicia for identifying the plurality of receptacles carried therein. In the illustrated embodiment, these indicia take the form of a grid-like series or pattern of lines separating the receptacles 26 into rows and columns. Additionally, a suitable viewing window 36 for viewing the color of the contents of each receptacle, in a fashion which will be described later, is provided in association with each through aperture 26. The associated viewing window 36 for each through aperture 26 and associated receptacle 12 is carried within the same square or rectangle defined by the grid pattern 34. Suitable letters or numbers 38 may also be utilized as the indicia for each receptacle and its associated viewing window.

Also associated with each receptacle 26 and its viewing window 36 is a novel optical means or structure in accordance with the invention to permit viewing of the color of the fluid carried within the associated receptacle 12. Referring now to FIG. 2, an exemplary optical means or structure is illustrated in association with one of the receptacles 12 and its associated viewing window 36.

An interior bottom wall or platform for receiving and supporting receptacles 12 is formed within the housing by a plate 40. This plate 40 extends substantially parallel with the top surface and is spaced above a bottom surface 42 of the housing 22 a sufficient distance to permit the mounting of additional components therebetween as will presently be described. Additional electrical heating elements to be described later may be provided for heating the plate 40, which accelerates the incubation process for the containers 12. The plate 40 may be provided with a suitable depression or seating surface 44 for each of the receptacles 12, to define a seated position of the receptacle 12 with respect to the incubator structure 22 and also to hold the cylindrical receptacle 12 in a substantially perpendicular or upright position with respect to the plate 40. In this regard, the receptacle 12 will be seen to define a longitudinal axis 48 which is preferably held by the receiving depression 44 substantially perpendicular with the plane of the heating plate 40.

Extending from a bottom portion of the plate 40 is a suitable light source, such as an incandescent lamp 50. It will be seen that lamp 50 also defines a longitudinal axis 52 which is mounted substantially perpendicular with the heating plate 40. In the illustrated embodiment, only one such lamp 50 is provided, substantially centrally located on the underside of plate 40, as best viewed in FIG. 5.

Referring to FIGS. 2, 3 and 4, the optical system of the invention includes a plurality of substantially similar sets of optical means or structures designated generally by the reference numeral 54, each set 54 being associated with one receptacle 12. These sets of optical means 54 are preferably substantially identical, whereby only one will be descirbed in detail with reference to FIGS. 2, 3 and 4.

In this regard, and referring first to FIG. 2, the optical means includes a first light transmisson means, such as a prism structure designated generally by the reference numeral 56. This prism structure 56 is configured and disposed for redirecting light from the light source or lamp 50 through the transparent portion 14 of the receptacle 12. Similarly, a second light transmission means, which also comprises a prism and is designated generally by reference numeral 58 is configured and disposed for redirecting light transmitted through the translucent portion of the receptacle 12 to the associated viewing window 36.

Referring briefly to FIG. 3, it is contemplated that the prisms 56 and 58 forming the light transmission means of FIG. 2 may alternatively be realized as an arrangement of mirrors with suitable mountings. In this regard, similar reference numerals with the suffix "a" are utilized in FIG. 3 to designate equivalent optical transmission means in the form of mirrors. It will be understood, however, that in all other respects, the structure and function of the embodiment of FIG. 3 is substantially identical with that of the preferred embodiment of the remaining figures of drawings which will be described in some further detail herein. Moreover, it is contemplated that a combination of one or more mirrors as shown in FIG. 3 and one or more prisms as shown in FIG. 2 may be selected and utilized without departing from the invention.

Returning to FIG. 2, the first prism 56 will be seen to be constructed of first and second prisms or prism segments 156 and 256 which are substantially identical and oppositely oriented. In order to transmit light from the lamp 50 at the bottom surface of plate 40 to the translucent portion of receptacle 12 which is located at the opposite or top surface of plate 40, these prism portions 156 and 256 are mounted to a through aperture 60 provided in the plate 40 therefor. The details of this mounting will be described later.

Referring also to FIG. 4, the first prism 156 includes a first face 62 which is substantially planar and oriented substantially at right angles to an imaginary radius 64 drawn from the longitudinal axis 52 of the light source 50 for receiving light therefrom. A second planar face 66 is formed substantially at right angles to the first face 62 and receives light therefrom by way of an intermediate or reflecting face 68. This latter reflecting face 68 is formed at a substantially 45 degree angle with respect to both faces 62 and 64 for redirecting light therebetween at substantially right angles.

As already noted, the second prism 256 is substantially identical in structure to first prism 156 and also includes a first substantially planar face or surface 72 which is oriented at substantially right angles to an imaginary radius 74 drawn from the longitudinal axis 48 of the receptacle 12. A similar second face or surface 76 is located at right angles to first face 72 and is in surface-to-surface contact with the face 66 of the first prism 156 and thus receives the light from said corresponding second face 66 of the first prism 156. A similar intermediate or reflecting face 78 is arranged at substantially a 45 degree angle with respect to both surfaces or faces 72, 76 for reflecting the light at substantially right angles therebetween.

It will be seen that both second faces 66 and 76 are circular and are defined by right conical extensions 166 and 176 of otherwise generally triangularly shaped solid bodies which comprise the prisms 156 and 256. Advantageously, these conical extensions interfit with the generally circular through aperture 60 to permit mounting of the respective prisms 156 and 256 to either side thereof for transmission of light through the plate 40. The thickness of extensions 166, 176 is preferably such that the faces 66, 76 substantially abut, when mounted to aperture 60. In this regard, faces 66 and 76 are preferably polished to facilitate light transmission therebetween.

Moreover, the conical extensions 166 and 176 permit relative rotation of the two prisms 156 and 256 so as to achieve the positioning of the faces 72 and 62 thereof along the respective radii, 64 and 74, of the light source or lamp 50 and receptacle 12, as previously noted. In this regard, and referring briefly to FIG. 5, it will be seen that an angle, for example, 80, 80' is formed between these respective radii 64, 74 or 64', 74', with respect to each optical means 54, 54' and its associated receptacle 12, 12'. Hence, the faces 62, 72 are oriented with a corresponding angle therebetween. Advantageously, the structure including the cylindrical extensions 166, 176 permits substantially identical prism elements to be utilized for each of the first optical transmission means 56 associated with the illustrated incubator 10.

The second optical transmission means 58 will now be seen to comprise a third prism. This third prism 58 is preferably a triangular solid prism structure substantially similar to that of the first and second prisms 156 and 256. Moreover, this third prism 58 includes a first face 82 which is substantially planar and oriented substantially at right angles to a radius 174 from the longitudinal axis of the receptacle 48. This radius 174 forms an extension of radius 74. The face 82 is additionally oriented substantially in a parallel and concentric alignment with respect to the face 72 of the prism 256, but generally to the opposite side of the receptacle 12. Accordingly, light transmitted through transparent portion 14 is received at the face 82 of prism 58 and redirected to a second face 86 thereof.

The second prism 58 includes an elongate columnar extension portion 186 which terminates in this second face 86, which is preferably configured for interfitting with one of windows 36 in the top surface 24 of the housing 22 of FIG. 1. A similar intermediate or reflecting face 88 is formed at substantially a 45 degree angle with respect to surfaces or faces 82, 86 for redirecting or reflecting light at substantially right angles therebetween. Moreover, it will be noted that the reflective face 88 is located in a substantially parallel and spaced apart plane with respect to reflective face 78 of prism 256 to thereby direct the light upwardly through the extension 186 and face 86, which, as described, is located in a plane parallel with, and in the illustrated embodiment generally coplanar with the top surface 24, at the window 36.

Referring again briefly to FIG. 3, it will be noted that one or more of the prisms 156, 256 and 58 may be replaced by a mirror 156a, 256a or 58a. These mirrors are provided with suitable mountings 110, 112 and 114 to achieve the same relative alignment for light transmission therebetween as that achieved generally by the alignment of reflective faces 68, 78 and 88 of the prisms of the preferred embodiment. That is, any one of the prisms of the preferred embodiment may be replaced by a mirror as illustrated in FIG. 3 which is oriented substantially similarly to the reflective face of the prism which it replaces. Such replacement is considered to form a part of the present invention.

Each of the first and second surfaces or faces of the respective prisms 156, 256 and 58 defines a center C and when assembled as indicated in FIG. 4, these faces are oriented generally as follows. The respective second faces 66 and 76 have their centers aligned and are located in parallel and preferably substantially abutting at the through aperture 60, while the corresponding first faces 62 and 72 are located in planes separated by an angle, such as the angle 80, defined between the respective two imaginary radius lines 64 and 74. Similarly, the first face 82 of the third prism 58 is in a plane parallel and spaced apart, that is, to the opposite side of the container 12, from the first face 72 of the prism 256. These two faces 72 and 82 also have their centers aligned.

Accordingly, since the respective reflective faces 78 and 88 of prisms 256 and 58 are substantially in parallel planes it will be seen that the three triangular solid prisms 156, 256 and 58 together collectively redirect light from the light source or lamp 50 through a succession of three substantially right angle bends. Hence, light is directed from the lamp 50 to and through the translucent portion of receptacle 12 and thence upwardly to the associated viewing window 36. In this regard, the travel of light through the optical system is indicated in FIG. 2 by the arrowheads on lines or radii 64, 164, 174 and 274, and ultimately reachng the edge of a viewer, indicated generally at 175. Once properly positioned the respective prism section may be secured or glued in place.

Figure 5:
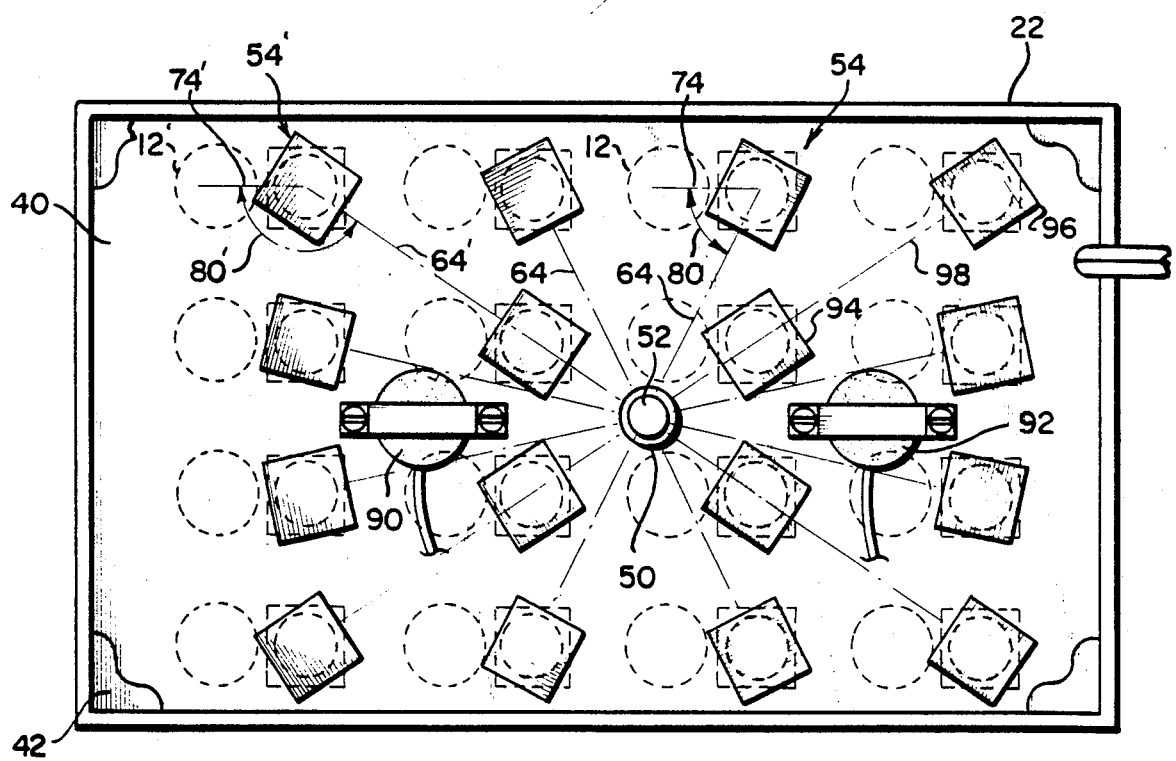
FIG. 5 is a bottom plan view of the incubator apparatus of FIG. 1, illustrating further features of the optical system of the invention, and particularly illustrating features of the embodiment of FIG. 2.

As best viewed in FIG. 5, the undersurface of heating plate 40 also preferably carries suitable heating elements, which in the illustrated embodiment take the form of a pair of electrical heating elements 90, 92. It will be noted that the respective first prism portions 156 are located in a radial array about the lamp 50. In order to have substantially similar illumination reaching each of these elements from the lamp 50, each first prism portion 156 has its first face or surface 62 oriented at substantially right angles to a radius from the axis or center 52 of the lamp 50. Additionally, it is noted that certain ones of the first prisms 156, for example, those prisms here designated 94 and 96 are located along the same or a common radius, here designated 98, from the lamp 50. Preferably, in such instances, the innermost of these two prisms 94 and 96 is made substantially shorter, that is, depending to a lesser extent from the undersurface of plate 40, to permit a substantial amount of light from lamp 50 to pass thereover and to the prism 96 located therebehind.

In accordance with a preferred form of the invention, one or more of the respective prisms 156, 256 and 58 may be colored, as by dyeing or tinting. This color is selected to bear a predetermined relationship to the color achieved by the test solution in the receptacle 12 when sterilization is unsuccessful, as described hereinabove. The color selected is such as to enhance the viewing of the expected color change, if any, of the test solution. In this regard, different solutions are generally provided for testing effectiveness as to different bacterial cultures. Accordingly, a number of different color changes, as from clear to a given color or from one given color to a second given color may occur as to various test solutions. Accordingly, this tinting or coloration of the prisms is selected to enhance viewing of the particular color change associated with a particular test solution.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. An incubator optical system for viewing a sterilization indicator, which sterilization indicator includes a receptacle having a translucent portion and being carried interiorly of an incubator, said optical system comprising: a light source, first light transmission means located intermediate said light source and said receptacle for redirecting light from said light source through said translucent portion of said receptacle; a viewing window located in an external surface of said incubator; and second light transmission means located on a side of said receptacle generally opposite said first light transmission means for redirecting light transmitted through said translucent portion of said receptacle to said viewing window; wherein said first light transmission means comprises first and second light redirecting means, said first light redirecting means being oriented for receiving light directly from said light source and for redirecting said received light to said second light redirecting means, and said second light redirecting means being oriented for redirecting light received from said first light redirecting means through said translucent portion of said receptacle.

2. An incubator optical system according to claim 1 wherein at least one of said first and second light transmission means comprises mirror means.

3. An incubator optical system according to claim 2 wherein at least one of said first and second light transmission means comprises prism means.

4. An incubator optical system according to claim 1 wherein said first and second light redirecting means comprise first and second prisms.

5. An incubator optical system according to claim 4 wherein said light source defines an axis, and wherein said first prism comprises a first face oriented substantially at right angles to a radius from said axis of said light source and a reflecting face oriented for redirecting light entering said first face toward said second prism.

6. An optical system according to claim 4 wherein said receptacle defines a longitudinal axis and wherein said second prism comprises a first face oriented substantially at right angles to a radius from said receptacle longitudinal axis and a reflecting face oriented for redirecting light received from said first prism toward said first face.

7. An incubator optical system according to claim 5 wherein said receptacle defines a longitudinal axis and wherein said second prism comprises a first face oriented substantially at right angles to a radius from said receptacle longitudinal axis and a reflecting face oriented for redirecting light received from said first prism toward said first face.

8. An incubator optical system according to claim 4 wherein said receptacle defines a longitudinal axis and wherein said second light transmission means comprises a third prism including a first face oriented substantially at right angles to a radius from said longitudinal axis of said receptacle, a second face oriented in a plane substantially parallel with said viewing window, and a reflecting face for redirecting light received at said first face to said second face.

9. An incubator optical system according to claim 7 wherein said receptacle defines a longitudinal axis and wherein said second light transmission means comprises a third prism including a first face oriented substantially at right angles to a radius from said longitudinal axis of said receptacle, a second face oriented in a plane substantially parallel with said viewing window, and a reflecting face for redirecting light received at said first face to said second face.

10. An incubator optical system according to claim 4 wherein said first, second and third prisms each comprises a substantially similar triangular prism, each having first and second faces formed at substantially right angles to each other and a reflecting face formed at substantially a 45 degree angle to said first and second faces for thereby redirecting light at substantially a right angle between said first and second faces.

11. An incubator optical system according to claim 7 wherein each of said prism first and second faces defines a center; and wherein respective second faces of each of said first and second prisms are aligned and located in parallel planes; said first faces thereof being located in planes separated by an angle corresponding to an imaginary angle defined between said radius of said light source and said radius of said receptacle.

12. An incubator optical system according to claim 11 wherein said first face of the third prism is oriented aligned with the center of, and in a plane parallel and spaced from the plane of, said first face of the second prism.

13. An incubator optical system according to claim 12 wherein the reflective face of the third prism is oriented substantially parallel to the reflective face of the second prism whereby the three triangular prisms together collectively redirect the light from said light source through a succession of three substantially right angle bends from said light source, to and through said translucent portion of said receptacle, to said viewing window.

14. An incubator for a sterilization indicator, which indicator includes a receptacle having a translucent portion and defining a longitudinal axis, said incubator comprising: a housing having a viewing surface; a plurality of through openings in said viewing surface, each for receiving one said receptacle therethrough to be carried interiorly of said housing; a like plurality of viewing windows, each associated with one said through opening and with the receptacle received therein; a light source; and a plurality of optical means, each associated with one of said viewing windows and the associated receptacle for transmitting light from the light source through said translucent portion of the associated receptacle and to the associated viewing window; each said optical means comprising first light transmission means located intermediate said light source and said receptacle for directing light from said light source through said translucent portion of said receptacle, and second light transmission means located on a side of said receptacle opposite said first light transmitting means for receiving light transmitted through said translucent portion of said receptacle and for directing said received light to said viewing window; and wherein each of said viewing windows is located in said viewing surface adjacent the associated one of said through openings therein.

15. An incubator according to claim 14 and further including a heating plate forming an interior bottom surface in said housing and for receiving and heating each of said receptacles.

16. An incubator according to claim 14 wherein said viewing surface is provided with indicia for identifying each of said viewing windows and its associated through opening.

17. An incubator optical system according to claim 14 wherein at least one of said first and second light transmission means comprises mirror means.

18. An incubator optical system according to claim 14 wherein at least one of said first and second light transmission means comprises prism means.

19. An incubator according to claim 14 wherein each said first light transmission means comprises first and second light redirecting means, said first light redirecting means being oriented for receiving light directly from said light source and for redirecting said received light to said second light redirecting means, and said second light redirecting means being oriented for redirecting light received from said first light redirecting means through said translucent portion of the associated receptacle.

20. An incubator according to claim 19 wherein said light source comprises a lamp mounted substantially centrally on an undersurface of a plate member carried internally of said housing, and said first and second light redirecting means comprise respective first and second prisms, each said first prism comprising a first face oriented substantially perpendicular to a radius from said lamp and a reflecting face for redirecting light entering said first face toward the associated second prism.

21. An incubator according to claim 20 wherein said plate includes a plurality of through openings for mounting respective associated first and second prisms to provide an optical path therebetween, each of said second prisms being located intermediate said viewing surface and said plate for directing said light received from the associated first prisms to the associated receptacle.

22. Apparatus according to claim 21 wherein each said receptacle defines a longitudinal axis and wherein each said second prism comprises a first face oriented substantially at right angles to a radius from the associated receptacle longitudinal axis and a reflecting face oriented for redirecting light received from said first prism towards said first face.

23. An incubator according to claim 20 wherein each said second light transmission means comprises a third prism including a first face oriented substantially parallel and spaced apart and along a common diameter of said receptacle with respect to said first face of the associated second prism, a second face oriented in a plane substantially parallel and spaced from the associated viewing window, and a reflecting face for redirecting light received at said first face to said second face.

24. An incubator according to claim 20 wherein predetermined ones of said first prisms are located along common radii from said lamp with predetermined others of said first prisms, and wherein the ones of said first prisms located more closely to said lamp are of reduced height with respect to the surface of said heating plate to permit transmission of light to those first prisms located farther from said lamp.

25. An incubator according to claim 20 wherein each of the associated first, second and third prisms comprises a substantially similar triangular prism, each having first and second faces formed at substantially right angles to each other and a reflecting face formed at substantially a 45 degree angle to said first and second faces for thereby redirecting light at substantially a right angle between said first and second faces.

26. An incubator according to claim 22 wherein said through apertures in said plate are substantially circular and wherein each of said first and second prisms includes a substantially right cylindrical base including a polished surface defining said second face thereof and insertable in said heating plate through aperture to thereby permit orientation of the respective first and second prism first faces with an angle therebetween corresponding to the angle defined between said radius from said lamp and said radius from the longitidinal axis of the associated receptacle.

27. An incubator according to claim 26 wherein the reflective face of each second prism is oriented substantially parallel to the reflective face of the associated second prism, whereby each three associated triangular prisms together collectively redirect the light from said lamp through a succession of three substantially right angle bends to and through said translucent portion of the associated receptacle and to the associated viewing window in said top surface.

28. An incubator according to claim 23 wherein at least one of said first, second and third prisms is a predetermined color.

29. An incubator for a sterilization indicator, which indicator includes a receptacle having a translucent portion and defining a longitudinal axis, said incubator comprising: a housing having a top surface; a plurality of through openings in said top surface, each for receiving one said receptacle therethrough to be carried interiorly of said housing; a like plurality of viewing windows, each associated with one said through opening and with the receptacle received therein; a light source; and a plurality of optical means, each associated with one of said viewing windows and the associated receptacle for transmitting light from the light source through said translucent portion of the associated receptacle and to the associated viewing window; each said optical means comprising first light transmission means located intermediate said light source and said receptacle for directing light from said light source through said translucent portion of said receptacle, and second light transmission means located on a side of said receptacle opposite said first prism means for receiving light transmitted through said translucent portion of said receptacle and for directing said received light to said viewing window; wherein said first light transmission means comprises first and second light redirecting means, said first light redirecting means being oriented for receiving light directly from said light source and for redirecting said received light to said second light redirecting means, and said second light redirecting means being oriented for redirecting light received from said first light redirecting means through said translucent portion of the associated receptacle.

* * * * *